United States Patent
Yotani

(10) Patent No.: US 9,216,366 B2
(45) Date of Patent: Dec. 22, 2015

(54) LIQUID CHROMATOGRAPHY COMPONENT

(71) Applicant: Sekisui Chemical Co., Ltd., Osaka (JP)

(72) Inventor: Takuya Yotani, Yamaguchi (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/050,482

(22) Filed: Oct. 10, 2013

(65) Prior Publication Data
US 2014/0034563 A1 Feb. 6, 2014

Related U.S. Application Data

(60) Continuation of application No. 13/305,002, filed on Nov. 28, 2011, now abandoned, which is a division of application No. 12/921,218, filed as application No. PCT/JP2009/056683 on Mar. 31, 2009, now abandoned.

(30) Foreign Application Priority Data

Mar. 31, 2008 (JP) .................................. 2008-093000

(51) Int. Cl.
*B01D 15/22* (2006.01)
*B01J 20/28* (2006.01)
(Continued)

(52) U.S. Cl.
CPC ........... *B01D 15/22* (2013.01); *B01J 20/28004* (2013.01); *G01N 30/14* (2013.01); *G01N 30/465* (2013.01); *G01N 30/603* (2013.01);
(Continued)

(58) Field of Classification Search
CPC  B01D 15/22; B01J 20/28004; B01J 2220/54; G01N 30/14; G01N 30/465; G01N 30/603; G01N 1/40; G01N 30/6069; G01N 2030/085; G01N 2030/146; G01N 2030/524
USPC .................... 210/635, 656, 659, 198.2, 502.1
See application file for complete search history.

(56) References Cited

U.S. PATENT DOCUMENTS 3,763,879 A   10/1973  Jaworek
4,350,595 A   9/1982   Gunkel
(Continued)

FOREIGN PATENT DOCUMENTS

JP   1-117765   8/1989
JP   2-262054   10/1990
(Continued)

OTHER PUBLICATIONS

Supplementary European Search Report issued Sep. 27, 2011 in corresponding European Patent Application No. EP 09 72 8577.
(Continued)

*Primary Examiner* — Ernest G Therkorn
(74) *Attorney, Agent, or Firm* — Wenderoth, Lind & Ponack, L.L.P.

(57) ABSTRACT

The present invention aims to provide a liquid chromatography component including a column and a prefilter, which is hard to cause an increase of supplied liquid pressure even when the measurement of a sample is repeated. The present invention is a liquid chromatography component, which includes: a column with filler particles filled therein; and a prefilter, the filler particles having an average particle size in the range of 2 to 20 μm, the prefilter having a filtering particle size in the range of 1/6 to 1/3 of the average particle size of the filler particles.

2 Claims, 1 Drawing Sheet

(51) Int. Cl.
*G01N 30/14* (2006.01)
*G01N 30/46* (2006.01)
*G01N 30/60* (2006.01)
*G01N 1/40* (2006.01)
*G01N 30/08* (2006.01)
*G01N 30/52* (2006.01)

(52) U.S. Cl.
CPC ............... *B01J2220/54* (2013.01); *G01N 1/40* (2013.01); *G01N 30/6069* (2013.01); *G01N 2030/085* (2013.01); *G01N 2030/146* (2013.01); *G01N 2030/524* (2013.01)

(56) References Cited

U.S. PATENT DOCUMENTS

| 4,451,365 A | 5/1984 | Sattler et al. |
| 4,457,846 A | 7/1984 | Munk |
| 4,565,632 A | 1/1986 | Hatch et al. |
| 4,737,284 A | 4/1988 | Hauke et al. |
| 5,693,223 A | 12/1997 | Yamada et al. |
| 5,714,074 A | 2/1998 | Karlsson et al. |
| 7,588,683 B2 | 9/2009 | Willis et al. |
| 2003/0064008 A1 | 4/2003 | Hage et al. |

FOREIGN PATENT DOCUMENTS

| JP | 5-203634 | 8/1993 |
| JP | 2006-138724 | 6/2006 |
| JP | 2006/189427 | 7/2006 |
| JP | 2006-227022 | 8/2006 |

OTHER PUBLICATIONS

PTO Translation No. 11-2761 of Yamazaki (Japanese Patent No. 2262054), Mar. 2011.
PTO Translation No. 11-276 of Yamazaki (Japanese Patent No. 2006/189427), Mar. 2011.
Snyder (Introduction to Modern Liquid Chromatography, John Wiley & Sons, Inc., New York, 1979, pp. 172-183).
Office Action for corresponding JP application No. 2010-505941 issued on May 29, 2012 (with partial translation).

LIQUID CHROMATOGRAPHY COMPONENT

REFERENCE TO RELATED APPLICATIONS

This application is a continuation of Ser. No. 13/305,002, filed Nov. 28, 2011, now abandoned, which, in turn, is division of Ser. No. 12/921,218, filed Oct. 27, 2010, now abandoned, which, in turn, is a 371 U.S. national stage of International Application No. PCT/JP2009/056683, filed Mar. 31, 2009.

TECHNICAL FIELD

The present invention relates to a liquid chromatography component including: a column with filler particles filled therein; and a prefilter, wherein the component is hard to cause an increase in the supplied liquid pressure even when the measurement of a sample is repeated. The present invention also relates to a liquid chromatography component including: a column with filler particles filled therein; and a prefilter, wherein the prefilter requires replacement at almost the same frequency as the column does. Further, the present invention relates to a liquid chromatography component including: a column with filler particles filled therein; and a prefilter, wherein the column and the prefilter are integrated with each other, require no complicated replacement operation, and show excellent separation performance.

BACKGROUND ART

In the fields of organic chemistry, biochemistry, medicine, and the like, liquid chromatography has been widely used for measurement or analysis of a component in a sample. In the medical field, for example, liquid chromatography has been employed for measuring hemoglobin A1c, which is an indicator for diabetes diagnosis. Hemoglobin A1c is glycosylated hemoglobin that has blood sugar chemically bound to an N-terminus of a β chain of hemoglobin. A proportion of hemoglobin A1C in hemoglobins, that is, a proportion of glycosylated hemoglobin in a sum of glycosylated hemoglobin and non-glycosylated hemoglobin is considered to reflect an average blood sugar level in a period of one to two months. Therefore, a hemoglobin A1c value (%) which represents the proportion of hemoglobin A1c in hemoglobins has been widely used as an indicator for diabetes diagnosis because the value does not show temporary fluctuation unlike a blood sugar level.

Filters such as an in-line filter for filtering foreign substances are located in a flow channel between a liquid chromatography sample-injection device to a column. Such filters are disposed in order to prevent foreign substances from clogging the channel, particularly the column body, and thereby changing the pressure of a supplied liquid. Particularly a prefilter, which is located on the upstream side of the column to filter foreign substrates, is an important filter linking directly to the column clogging caused by the foreign substances.

Examples of the foreign substances, which are captured on the filters, include: those contained in a mobile phase, a reaction reagent, and the like; those from a part of an analyzer, such as a feed pump; and those derived from a sample. These foreign substances are adsorbed on the surface of filler particles filled in the column or to a detector cell, and as a result, may adversely affect the measurement or analysis. Accordingly, there have been developed various filters for efficiently capturing these foreign substances.

However, when the filtration efficiency of the filters is increased in order to more efficiently capture the foreign substances, the foreign substances may more easily clog the filters to cause the change in the supplied liquid pressure. Particularly when a large number of samples are continuously measured as in analysis of hemoglobins or when a sample high in foreign substances like a hemolyzed blood sample is measured, the foreign substances clog the filter and often cause an increase in the supplied liquid pressure. The change in the supplied liquid pressure may lead to a failure in accurate and quick measurement or analysis of the sample.

Examples of a common method of suppressing the increase in the supplied liquid pressure, caused by clogging of the filter, include a method of increasing a filtration area of the filter, a method of increasing a porosity of the filter, and a method of modifying a configuration of the filter. However, when the filtration area or the porosity of the filter is increased too much, the sample or the mobile phase in the filter may be diffused too much, which reduces the accuracy of the measurement or analysis.

As an example of modifying a configuration of the filter, Patent Document 1 discloses a method of using a two-layer filter composed of layers with different pore sizes. Patent Document 2 discloses a method of using a two-layer structure composed of a filter paper sheet and a filter. These methods are designed to prevent the clogging attributed to the foreign substances by a combination use of the two different filters without decreasing the filtration efficiency for the foreign substances. However, these ideas have been established by taking only the filter into consideration, and no studies have been made covering the column where the clogging attributed to the foreign substances poses a problem as in the filter.

For example, a column for analysis of hemoglobins, which is used for measuring a hemoglobin A1c value, is usually replaced each time after the measurement of 1500 to 3000 samples is completed, although depending on the number of samples guaranteed by a manufacturer. In contrast to this, the prefilter, which is located on the upstream side of the column, is usually replaced each time after the measurement of hundreds of samples is completed. Thus, the filters require the replacement more often than the column does, which is a significant burden in terms of operation and cost.

Patent Document 1: Japanese Kokai Publication No. Hei-02-262054 (JP-A Hei-02-262054)
Patent Document 2: Japanese Kokai Publication No. Hei-05-203634 (JP-A Hei-05-203634)

DISCLOSURE OF THE INVENTION

Problems to be Solved by the Invention

The present invention aims to provide a liquid chromatography component including: a column with filler particles filled therein; and a prefilter, wherein the component is hard to cause an increase in supplied liquid pressure even if the measurement of a sample is repeated, and wherein the prefilter requires replacement at almost the same frequency as the column does. Further, the present invention relates to a liquid chromatography component including: a column with filler particles filled therein; and a prefilter, wherein the column and the prefilter are integrated with each other, require no complicated replacement operation, and show excellent separation performance.

The present invention is a liquid chromatography component, which includes: a column; and a prefilter, the filler particles having an average particle size in the range of 2 to 20

μm, the prefilter having a filtering particle size in the range of ⅙ to ⅓ of the average particle size of the filler particles.

The present invention is described in detail below.

The liquid chromatography component of the present invention includes a column and a prefilter.

In the column, the filler particles are filled in a cylindrical container.

Examples of the filler particles include: inorganic particles such as silica; organic particles comprising resins such as a styrene-divinyl benzene copolymer; and these particles with a surface having an ion-exchange group bonded thereto.

The lower limit of the average particle size of the filler particles is 2 μm, and the upper limit thereof is 20 μm. If the average particle size of the filler particles is smaller than 2 μm, the supplied liquid pressure in the column may become too high, and a burden on the analyzer may increase too much. If the average particle size of the filler particles is larger than 20 μm, the separation performance is degraded, and for example, if the particles with such an average particle size are used in measurement of hemoglobin A1c, hemoglobins may be insufficiently separated. The lower limit of the average particle size of the filler particles is preferably 6 μm, and the upper limit thereof is preferably 12 μm.

The average particle size of the filler particles can be measured with a laser diffraction-type particle size distribution measuring apparatus.

The lower limit of the inner diameter of the column is preferably 2.0 ram, and the upper limit thereof is preferably 6.0 mm. If the inner diameter of the column is smaller than 2.0 mm, the linear velocity of a mobile phase flowing inside the column may become too high, and the supplied liquid pressure may increase too much. If the inner diameter of the column is larger than 6.0 mm, the sample or the mobile phase inside the column may be diffused too much, possibly resulting in deterioration of the separation performance. The lower limit of the inner diameter of the column is more preferably 3.0 mm, and the upper limit thereof is more preferably 5.0 mm.

The lower limit of the length of the column is preferably 10 mm, and the upper limit thereof is preferably 50 mm. If the column is shorter than 10 mm, the separation performance may be degraded along with a decrease in the number of theoretical plates. If the column is longer than 50 mm, elution of a sample may require a longer time to extend the measurement time, or the supplied liquid pressure may increase. The lower limit of the length of the column is more preferably 15 mm, and the upper limit thereof is more preferably 40 mm.

It is preferable that a filter is disposed on each of the upstream and downstream sides of the column, thereby preventing the filler particles filled in the column from leaking from a cylindrical container. These filters are not disposed with the view of capturing foreign substances, and it is sufficient if the filters can prevent the leakage of the filler particles from the cylindrical container. When the below-mentioned prefilter is integrated with the column and located extremely close thereto, the filter on the upstream side may not be disposed, and instead, the prefilter may prevent the filler particles filled in the column from leaking from the cylindrical container.

The prefilter may be made of paper, resin, metal, and the like. Particularly preferably used is a stainless-steel filter having a three-layer structure composed of layers with different pore sizes, disclosed in Japanese Kokai Publication No. 2006-189427 (JP-A 2006-189427).

The filtering surface of the prefilter may have a circular shape, or any other shape.

The prefilter has a filtering particle size in the range of ⅙ to ⅓ of the average particle size of the filler particles. Foreign substances that are not captured by the prefilter and pass therethrough are not captured in the column either to pass through spaces between the filler particles inside the column. As a result, clogging is suppressed in the prefilter and the column. If the filtering particle size of the prefilter is smaller than ⅙ of the average particle size of the filler particles, the clogging of the prefilter may occur much earlier than that of the column, so that the prefilter may require replacement frequently. If the filtering particle size of the prefilter is larger than ⅓ of the average particle size of the filler particles, the clogging of the prefilter may occur less often, but foreign substances may clog up spaces between the filler particles inside the column, possibly resulting in deterioration of the separation performance. Preferably, the filtering particle size is in the range of ⅕ to ⅓ of the average particle size of the filler particles.

The filtering particle size means a particle size at which, when standard particles with a known particle size are filtered through the prefilter, the capture rate of the standard particles is 95% or higher. As the standard particles, commercially available polystyrene standard particles produced by Moritex Corp. can be used.

The capture rate (%) of the standard particles is measured in the following procedures.

The prefilter is connected to a liquid chromatograph, and purified water is allowed to flow as a mobile phase. The standard particle sample is allowed to flow at a general feed speed, for example, 1.7 mL/min. Then, the peak area (1) of the obtained chromatogram is calculated. The peak area (1) reflects the amount of the standard particles having passed through the prefilter without being captured thereby.

Next, the prefilter is replaced with a pipe, and then the same standard particle sample is allowed to follow. Then, the peak area (2) of the obtained chromatogram is calculated. The peak area (2) reflects the amount of the standard particle having being supplied.

Based on the peak area (1) and the peak area (2), the capture rate (%) of the standard particles is calculated from the following formula.

$$\text{Capture rate (\%) of standard particles} = 100 - (\text{peak area (1)/peak area (2)}) \times 100$$

The lower limit of the effective filtration area of the prefilter is preferably 7 mm$^2$, and the upper limit thereof is preferably 80 mm$^2$. If the effective filtration area of the prefilter is smaller than 7 mm$^2$, the clogging of the prefilter may occur more often because the range where the foreign substances can be captured is narrow. If the effective filtration area of the prefilter is larger than 80 mm$^2$, the sample or the mobile phase inside the prefilter may be diffused too much, possibly resulting in degradation of the separation performance. The lower limit of the effective filtration area of the prefilter is more preferably 12 mm$^2$, and the upper limit thereof is more preferably 65 mm$^2$.

The lower limit of the thickness of the prefilter is preferably 0.1 mm, and the upper limit thereof is preferably 10 mm. If the thickness of the prefilter is smaller than 0.1 mm, the clogging of the prefilter may occur more often. If the thickness of the prefilter is larger than 10 mm, the sample or the mobile phase inside the prefilter may be diffused too much, possibly resulting in deterioration of the separation performance. The lower limit of the thickness of the prefilter is more preferably 0.2 mm, and the upper limit thereof is more preferably 3 mm.

The lower limit of the porosity of the prefilter is preferably 60%. If the porosity of the prefilter is smaller than 60%, the clogging of the prefilter may occur more often. The lower limit of the porosity of the prefilter is more preferably 65%. The upper limit of the porosity of the prefilter is preferably 90% since a prefilter with an excessively high porosity possibly does not satisfy the desired filtering particle size.

In the liquid chromatography component of the present invention, the column and the prefilter may be disposed independently, or may be integrally disposed within a single cylindrical container. In each case, the component is jointed to a pipe of the analyzer such that the prefilter is located on the upstream side of the column.

When being disposed independently, the column and the prefilter can be replaced independently. When being integrally disposed, the column and the prefilter can be replaced together, so that the replacement operation becomes easier. Further, the integrated column-prefilter occupies less space, so that the analyzer can be downsized. Further, when the column and the prefilter are integrally disposed, the distance between the two is substantially zero, so that the sample and the mobile phase is hardly diffused between the column and the prefilter. As a result, the separation performance is improved, and the measurement time can be more shortened.

The cylindrical container comprises a material with a proper strength, and can accommodate the filler particles, or both of the filler particles and the prefilter. Examples of the material for the cylindrical container include metals such as stainless steel and titanium, resins such as fluorine resin and polyether ether ketone, and glass materials.

The cylindrical container may be a single-piece one or a disassemblable one.

It is preferable that the prefilter or the cylindrical container is subjected to a surface treatment, thereby preventing non-specific adsorption to the surface. The surface treatment means a chemical and/or a physical treatment that is provided on a surface in order to modify the surface properties. Specific examples of the surface treatment include: surface modification by a thermal or acid oxidation reaction; and a blocking treatment of covering the surface with a substance having desired characteristics, such as a hydrophilic substance and a hydrophobic substance. Proteins such as bovine serum albumin, globulin, lactoferrin, and skim milk; silicone; and fluorine resins can be used as the substance used in the blocking treatment.

According to the present invention, the life of the prefilter becomes very long by adjustment of a combination of the average particle size of the filler particles filled in the column and the filtering particle size of the prefilter. Therefore, the replacement frequency of the column can be made equivalent to that of the prefilter.

Since the replacement frequency of the column is equivalent to that of the prefilter, the prefilter, which is located on the upstream side of the column, requires no replacement during a period of use of the column. Further, the column and the prefilter are integrally disposed, so that the replacement operation of the two can be made easier. Also, since the integrated column-prefilter occupies less space, the analyzer can be downsized.

The present invention also includes a liquid chromatography component, wherein a column with filler particles filled therein and a prefilter body are integrally disposed within a single cylindrical container.

For example, when the liquid chromatography component includes the prefilter and the column, the replacement frequency of the column can be made equivalent to that of the prefilter.

The column and the prefilter, which require replacement at almost the same frequency, are integrally disposed within a single cylindrical container, whereby the column and the prefilter can be replaced in a single replacement operation. Thus, the replacement operation can be efficiently carried out. In addition, the column and the prefilter are disposed with substantially no distance therebetween, so that the sample or the mobile phase is hardly diffused between the column and the prefilter. As a result, the separation performance is improved, and the measurement time can be more shortened.

DESCRIPTION OF THE PREFERRED EMBODIMENTS

Effect of the Invention

Figure 1:
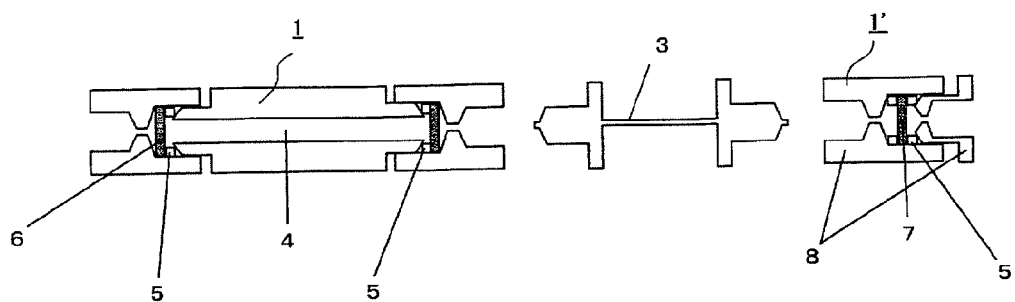
FIG. 1 shows one example of a liquid chromatography component of the present invention, in which the column and the prefilter are independently disposed.

The present invention provides a liquid chromatography component including a column and a prefilter, wherein the component is hard to cause an increase in supplied liquid pressure even if the measurement of a sample is repeated, and wherein the prefilter requires replacement at almost the same frequency as the column does. The present invention also provides a liquid chromatography component including a column and a prefilter, wherein the column and the prefilter are integrated with each other, require no complicated replacement operation, and show excellent separation performance.

BEST MODE FOR CARRYING OUT THE INVENTION

The aspects of the present invention are described below in more detail based on examples. The present invention is not limited to the examples.

Example 1

(1) Preparation of Prefilter

A sintered stainless-steel fiber filter sheet with a thickness of 0.4 mm and a porosity of 70% was punched into a circular shape with a diameter of 9.0 mm to give a sintered stainless-steel fiber filter with a filtration area of 63.59 $mm^2$. The sintered stainless-steel fiber filter sheet had a three-layer structure composed of: a filter layer (outer layer 1) with a pore diameter of 12 μm and a thickness of 0.1 mm; a filter layer (inner layer) with a pore diameter of 3 μm and a thickness of 0.2 mm; and a filter layer (outer layer 2) with a pore diameter of 12 μm and a thickness of 0.1 mm, stacked in this order. The obtained filter was subjected to a blocking treatment with bovine serum albumin, thereby preventing non-specific adsorption of hemoglobins.

The surface-treated filter was secured with a polytetrafluoroethylene packing and then housed in a polyether ether ketone holder with a thread portion that can be connected to a channel. Thus, a prefilter was prepared. The prefilter had an effective filtration area, which is an area except for the packing-contacting area, of 50.24 $mm^2$.

The obtained prefilter was measured for filtering particle size and found to be 3 μm.

(2) Preparation of Column

A mixture containing tetraethylene glycol dimethacrylate (product of Shin-Nakamura Chemical Co., Ltd.) 300 g, triethylene glycol dimethacrylate (product of Shin-Nakamura Chemical Co., Ltd.) 100 g, and benzoyl peroxide (product of Kishida Chemical Co., Ltd.) 1.0 g was added to a 3% aqueous solution of polyvinyl alcohol (product of Nippon Synthetic Chemical Industry Co., Ltd.). Under stirring, the resulting mixture in a reaction vessel was polymerized under nitrogen atmosphere at 80° C. for one hour.

Next, as a monomer containing an ion-exchange group, 2-methacrylamide-2-methylpropanesulfonic acid (product of TOAGOSEI CO., LTD.) 100 g, polyethylene glycol methacrylate (product NOF CORPORATION, ethylene glycol chain n=4) 100 g were dissolved in ion-exchanged water. This mixture was further added into the above-mentioned reaction vessel after one hour-polymerization, and then polymerized at 80° C. for 2 hours under stirring and nitrogen atmosphere. The obtained polymer composition was washed with water and acetone, thereby yielding ion-exchange group-containing particles.

The obtained particles 10 g were immersed in an ozone water 300 mL with a dissolved ozone gas concentration of 100 ppm and then stirred for 30 minutes. After completion of the stirring, the mixture was centrifuged with a centrifuge (Himac CR20G, produced by Hitachi, Ltd.), thereby removing supernatant fluid. This process was repeated twice to obtain filler particles.

The average particle size and the CV value of the obtained filler particles were measured with the laser diffraction-type particle size distribution measuring apparatus, and were found to be values of 10 μm and 14%, respectively.

The obtained filler particles were charged into a cylindrical container with 4.6 mm in inner diameter and 20 mm in length. Thus, a column was prepared. A filter (the reference number 6 in FIGS. 1 and 2) with 6.5 mm in diameter, prepared by punching of the above-mentioned sintered stainless-steel fiber filter, was disposed on each of the upstream and downstream sides of the column, so as to prevent the filler particles from leaking from the cylindrical container.

(3) Production of Liquid Chromatography Component

The obtained prefilter and column were disposed as illustrated in FIG. 1 to produce a column/prefilter discrete-type liquid chromatography component. Hereafter, the liquid chromatography component having the configuration of FIG. 1 is referred to as a discrete-type liquid chromatography component.

Figure 2:
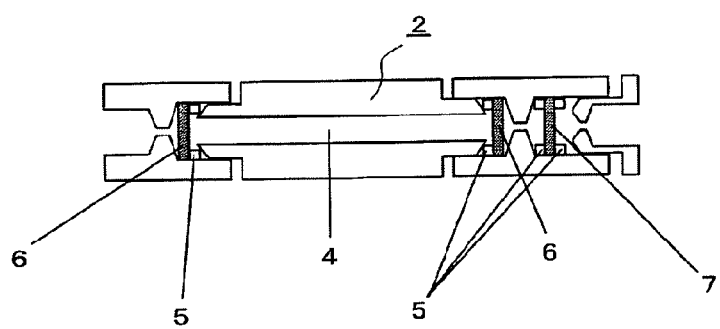
FIG. 2 shows one example of a liquid chromatography component of the present invention, in which the column and the prefilter are integrally disposed within a single cylindrical container.

The obtained prefilter and column were disposed as illustrated in FIG. 2 to produce a column/prefilter integrated-type liquid chromatography component. Hereafter, the liquid chromatography component having the configuration of FIG. 2 is referred to as an integrated-type liquid chromatography component.

Examples 2 to 6, Comparative Examples 1 and 2

Discrete-type liquid chromatography components (FIG. 1) and integrated-type liquid chromatography components (FIG. 2) were produced in the same manner as in Example 1, except that the prefilters and the columns shown in Table 1 were used.

The effective filtration area of the prefilter was adjusted by a change in the diameter of the punching mold. The filtering particle size of the prefilter was adjusted by a change in the pore diameter of the inner layer of the filter. The average particle size of the filler particles was adjusted by a change in the rotation speed of the stirring upon the polymerization.

TABLE 1

|  |  | Example 1 | Example 2 | Example 3 | Example 4 | Example 5 | Example 6 | Comparative Example 1 | Comparative Example 2 |
|---|---|---|---|---|---|---|---|---|---|
| Prefilter | Effective filtration area (mm$^2$) | 50.24 | 50.24 | 50.24 | 23.75 | 50.24 | 50.24 | 50.24 | 50.24 |
|  | Thickness (mm) | 0.4 | 0.4 | 0.4 | 0.4 | 0.4 | 0.4 | 0.4 | 0.4 |
|  | Porosity (%) | 70 | 70 | 70 | 70 | 70 | 70 | 70 | 70 |
|  | Filtering particle size (μm) | 3.0 | 2.5 | 1.8 | 3.0 | 2.0 | 4.0 | 5.0 | 1.4 |
| Column | Average particle size of filler particles (μm) | 10.0 | 10.0 | 10.0 | 10.0 | 6.0 | 12.0 | 10.0 | 10.0 |
|  | Inner diameter of column (mm) | 4.6 | 4.6 | 4.6 | 4.6 | 4.6 | 4.6 | 4.6 | 4.6 |
|  | Length of column (mm) | 20.0 | 20.0 | 20.0 | 20.0 | 20.0 | 20.0 | 20.0 | 20.0 |

(Evaluation)

(1) Evaluation of Supplied Liquid Pressure

Any of the discrete-type liquid chromatography component produced in Examples and Comparative Examples to the following system was jointed to the following systems, and thereby setting up a liquid chromatography analyzer.

Feed pump: LC-20AD (produced by Shimadzu Corp.)
Auto sampler: SIL-20AC (produced by Shimadzu Corp.)
Detector: SPD-M20A (produced by Shimadzu Corp.)
Column oven: CTO-20AC (produced by Shimadzu Corp.)

A total of 3000 samples were successively measured with this liquid chromatography analyzer under the following analysis conditions.

Eluent:
   first solution 50 mmol/L phosphate buffer (pH 5.3)
   second solution 250 mmol/L phosphate buffer (pH 8.0) containing 0.05% by weight of polyoxyethylene (20) sorbitan monolaurate (produced by Wako Pure Chemical Industries, Ltd.)
Measuring time: 50 seconds
Flow rate: 1.7 mL/min
Column temperature: 40° C.
Detection wavelength: 415 nm Sample: whole blood from a healthy human was diluted 201-fold with a hemolysing agent (phosphate buffer (pH 7.0) containing 0.1% by weight of polyoxyethylene (10) octylphenyl ether (produced by Wako Pure Chemical Industries, Ltd.)) to yield a sample to be evaluated.
Amount of sample injection: 10 μL After completion of the continuous analysis of the 3000 samples, the pressure when the first solution of the eluent was supplied into each of the column and the prefilter was measured. The pressure increase in the first solution was calculated from the following formula. When the pressure increase in both of the column and the prefilter is 0.3 MPa or lower, the case is evaluated as "O". When the pressure increase in either the column or the prefilter exceeds 0.3 MPa, the case is evaluated as "x".

Table 2 shows the results.

Pressure increase=(Pressure of supplied liquid after continuous analysis of 3000 samples)−(Pressure of supplied liquid before sample analysis)

TABLE 2

|  | Pressure increase in column (MPa) | Pressure increase in prefilter (MPa) | Evaluation |
|---|---|---|---|
| Example 1 | 0 | 0 | O |
| Example 2 | 0 | 0.1 | O |
| Example 3 | 0 | 0.3 | O |
| Example 4 | 0 | 0 | O |
| Example 5 | 0 | 0.2 | O |
| Example 6 | 0 | 0 | O |
| Comparative Example 1 | 0.6 | 0 | X |
| Comparative Example 2 | 0 | 0.8 | X |

Table 2 shows that when the liquid chromatography components of Examples 1 to 6 were used, the pressure increase in each of the prefilter and the column was 0.3 MPa or lower in every case. Even after the continuous analysis of the 3000 samples, the pressure was hardly changed in each of the column and the prefilter. In Examples 2, 3, and 5, the pressure of the first solution in the prefilter was slightly increased but in insignificant range.

In contrast to this, the pressure increase was observed in the column when the liquid chromatography component of Comparative Example 1 was used. The reason for this is considered that the combination of the column and the prefilter was not suitable and that foreign substances that had passed through the prefilter without being captured clogged up spaces of the filler particles inside the column during the repeated measurement. When the liquid chromatography component of Comparative Example 2 was used, an increase in the pressure of the first solution was observed in the prefilter. The reason for this is considered that excessive foreign substances were captured by the prefilter, and the captured substances caused clogging of the prefilter during the repeated measurement.

(2) Durability Evaluation

The discrete-type or integrated-type liquid chromatography component produced in Example 4 was jointed to the following systems, thereby setting up a liquid chromatography analyzer.
Feed pump: LC-20AD (produced by Shimadzu Corp.)
Auto sampler: SIL-20AC (produced by Shimadzu Corp.)
Detector: SPD-M20A (produced by Shimadzu Corp.)
Column oven: CTO-20AC (produced by Shimadzu Corp.)

With these liquid chromatography analyzers, the hemoglobin A1c value was continuously measured under the following analysis conditions, and the durability was evaluated.
Table 3 shows the results (HbA1c value).
Eluent:
first solution 50 mmol/L phosphate buffer (pH 5.3)
second solution 250 mmol/L phosphate buffer (pH 8.0) containing 0.05% by weight of polyoxyethylene (20) sorbitan monolaurate (produced by Wako Pure Chemical Industries, Ltd.).
Measuring time: 50 seconds
Flow rate: 1.7 mL/min
Column temperature: 40° C.
Detection wavelength: 415 nm
Sample to be loaded: whole blood from a healthy human was diluted 201-fold with a hemolyzing agent (phosphate buffer (pH 7.0) containing 0.1% by weight of polyoxyethylene (10) octylphenyl ether (produced by Wako Pure Chemical Industries, Ltd.)) to prepare a sample to be loaded.
Sample to be evaluated: each of glyco Hb control levels 1 and 2 (produced by Sysmex International Reagents Co., Ltd.) was dissolved in an water for injection 200 μL, and then diluted 101-fold with a phosphate buffer (pH 7.0) containing 0.1% by weight of polyoxyethylene (10) octylphenyl ether (produced by Wako Pure Chemical Industries, Ltd.)) to prepare a sample to be evaluated.

After the measurement of every 200 samples to be loaded, 3 samples to be evaluated were measured, and average values thereof were used for the evaluation.
Amount of sample injection: 10 μL

TABLE 3

| The number of sample | Column/prefilter discrete-type Hemoglobin A1c value (%) | | Column/prefilter integrated-type Hemoglobin A1c value (%) | |
|---|---|---|---|---|
| | Level 1 | Level 2 | Level 1 | Level 2 |
| 0 | 5.2 | 10.2 | 5.2 | 10.2 |
| 200 | 5.2 | 10.2 | 5.2 | 10.2 |
| 400 | 5.2 | 10.3 | 5.2 | 10.2 |
| 600 | 5.3 | 10.2 | 5.2 | 10.2 |
| 800 | 5.2 | 10.2 | 5.2 | 10.2 |
| 1000 | 5.2 | 10.2 | 5.2 | 10.2 |
| 1200 | 5.3 | 10.2 | 5.3 | 10.3 |
| 1400 | 5.2 | 10.2 | 5.2 | 10.2 |
| 1600 | 5.2 | 10.3 | 5.2 | 10.2 |
| 1800 | 5.2 | 10.2 | 5.2 | 10.2 |
| 2000 | 5.2 | 10.1 | 5.2 | 10.1 |
| 2200 | 5.2 | 10.2 | 5.2 | 10.2 |
| 2400 | 5.2 | 10.2 | 5.2 | 10.2 |
| 2600 | 5.3 | 10.2 | 5.3 | 10.2 |
| 2800 | 5.2 | 10.3 | 5.2 | 10.3 |
| 3000 | 5.2 | 10.2 | 5.2 | 10.2 |
| Avg. | 5.22 | 10.21 | 5.21 | 10.21 |
| SD | 0.04 | 0.05 | 0.03 | 0.04 |
| CV | 0.77 | 0.49 | 0.66 | 0.43 |

As shown in Table 3, each of the discrete-type and the integrated-type liquid chromatography components in Example 4 exhibited excellent durability.

INDUSTRIAL APPLICABILITY

The present invention can provide the liquid chromatography component composed of a column and a prefilter, wherein the component is hard to cause an increase in supplied liquid pressure even when the measurement of a sample is repeated, and wherein the prefilter requires replacement at almost the same frequency as the column does.

The present invention can provide the liquid chromatography component including a column and a prefilter, wherein the component is hard to cause an increase in supplied liquid pressure even when the measurement of a sample is repeated, and wherein the prefilter requires replacement at almost the same frequency as the column does.

The present invention also provides the liquid chromatography component including a column and a prefilter, wherein the column and the prefilter are integrated with each other, require no complicated replacement operation, and show excellent separation performance.

BRIEF DESCRIPTION OF THE DRAWINGS

FIG. 1 is a schematic view showing an example of a liquid chromatography component of the present invention, wherein a column and a prefilter are independently disposed.

FIG. 2 is a schematic view showing an example of a liquid chromatography component of the present invention, wherein a column and a prefilter are integrally disposed.

EXPLANATION OF SYMBOLS

1 Discrete-type liquid chromatography component (Column part)
1' Discrete-type liquid chromatography component (Prefilter part)
2 Integrated-type liquid chromatography component
3 Joint pipe
4 Part filled with filler particles in column
5 Polytetrafluoroethylene packing
6 Filter for preventing leakage of filler particles
7 Prefilter
8 Polyether ether ketone holder

The invention claimed is:

1. A liquid chromatography component,
which comprises:
a column with filler particles filled therein; and
a prefilter;
wherein the prefilter is located on the upstream side of the column,
wherein the prefilter and the column are joined via a joint pipe,
wherein the filler particles have an average particle size in the range of 2 to 20 μm, and
wherein the prefilter has a filtering particle size in the range of ⅙ to ⅓ of the average particle size of said filler particles and the prefilter has an effective filtration area of 23.75 to 50.24 mm$^2$.

2. A liquid chromatography component,
which comprises:
a column with filler particles filled therein; and
a prefilter,
wherein the prefilter is located on the upstream side of the column,
wherein the column and the prefilter are integrally disposed within a single cylindrical container with no distance therebetween, and
wherein the prefilter has a filtering particle size in the range of ⅙ to ⅓ of the average particle size of said filler particles and the prefilter has an effective filtration area of 23.75 to 50.24 mm$^2$.

* * * * *